United States Patent [19]

McElligott, Jr.

[11] Patent Number: 4,549,993

[45] Date of Patent: Oct. 29, 1985

[54] PURIFICATION OF CRUDE, LIQUID ORGANOSULFONYL CHLORIDE

[75] Inventor: Paul J. McElligott, Jr., Abington, Pa.

[73] Assignee: Pennwalt Corporation, Philadelphia, Pa.

[21] Appl. No.: 609,680

[22] Filed: May 14, 1984

Related U.S. Application Data

[63] Continuation-in-part of Ser. No. 597,302, Apr. 6, 1984, abandoned.

[51] Int. Cl.$^4$ ........................................... C07C 143/70
[52] U.S. Cl. ................................................ 260/543 R
[58] Field of Search ..................................... 260/543 R

[56] References Cited

U.S. PATENT DOCUMENTS 3,626,004 12/1971 Guertin ............................ 260/543 R
3,993,692 11/1976 Giolito et al. ..................... 260/543 R
4,280,966 7/1981 Hubenett .......................... 260/543 R

OTHER PUBLICATIONS

*Hackh's Chemical Dictionary*, 4th Ed., (1969), McGraw-Hill, Publ. at p. 601.

Primary Examiner—Natalie Trousof
Assistant Examiner—L. Hendriksen

[57] ABSTRACT

Crude, liquid organosulfonyl chloride is purified by first scrubbing the crude liquid with an aqueous hydrochloric acid solution, separating the scrubbing solution and then subjecting the scrubbed organosulfonyl chloride to vacuum stripping while sweeping the material being stripped with an inert gas.

11 Claims, No Drawings

PURIFICATION OF CRUDE, LIQUID ORGANOSULFONYL CHLORIDE

BACKGROUND OF THE INVENTION

This application is a continuation-in-part of corresponding application Ser. No. 597,302 filed Apr. 6, 1984, now abandoned.

This invention relates to a process, preferably continuous, for removing impurities from crude liquid organosulfonyl chlorides in a two step operation. The crude liquid product is first subjected to a scrubbing operation with a clean, aqueous hydrochloric acid solution to remove organosulfonic acid and then the scrubbed product is subjected to vacuum stripping to vaporize volatiles including, for example, mercaptans, chlorine, sulfides and water while the volatiles are swept with an inert gas to rapidly remove vapors produced during the stripping operation.

Organosulfonyl chlorides of high purity are needed because many of the uses for such products will not tolerate impurities. For example, they are used in the production of cotton fibers, drugs such as steroids, and general organic chemicals. The organic sulfonyl chlorides are also used in the preparation of several large-scale products sensitive to acid by-products, such as the production of herbicides.

PRIOR ART

In priorart methods for producing organosulfonyl chlorides (hereinafter represented by methyl sulfonyl chloride or MSC) the by-product organosulfonic acid (hereinafter represented by methane sulfonic acid or MSA) is present at levels greater than 1000 parts per million (ppm) and is not completely removed in the usual purification steps.

U.S. Pat. No. 3,626,004 discloses the preparation of MSC by direct reaction of methyl mercaptan and chlorine in 36% aqueous hydrochloric acid. Since HCl builds up a steady state concentration of impurities, the MSC isolated from the reaction is still highly contaminated because no extraction of impurities with clean aqueous HCl occurs. Topping of the water-containing product at elevated temperature (75° C.), as taught in this patent, promotes the hydrolysis of MSC causing the impurity level of the product to remain high. In the production of alkyl sulfonyl chlorides having from 1—4 carbon atoms in the alkyl group, the crude product is recovered as a bottom liquid phase containing major amounts of water, MSA and aqueous HCl. Vaporization of MSA and water from MSC is extremely difficult, even under vacuum, without the formation of additional undesirable by-products, because MSA and water form firmly bound hydrates wherein the acid and water have relatively high boiling points. The purification procedure of U.S. Pat. No. 3,626,004 does not overcome this problem.

U.S. Pat. No. 3,993,692, discloses a method of preparing MSC similar to the above mentioned U.S. Pat. No. 3,626,004. Separation of some impurities before stripping is carried out by cooling the crude product and phase separating MSC. Some product is also recovered from the contaminated aqueous HCl phase by extraction with benzene. However, the product still contains over 0.5% impurities.

U.S. Pat. No. 4,280,966 discloses a process in which MSC is coproduced with concentrated HCl. As the crude product is generated, it is taken overhead and some of the more volatile components such as HCl, are separated by a "cyclone" gas separator. This leaves some HCl as well as less volatile water and MSA in the crude MSC product. The crude product may then be subjected to a purification operation at reduced pressure with an inert sweep gas to purge out HCl. The product still contains an undesirable amount of impurities.

STATEMENT OF THE INVENTION

The present invention is directed to a process for purifying a crude liquid organosulfonyl chloride product recovered from its manufacturing process, or otherwise found in a similar contaminated condition, wherein said crude product is first subjected to scrubbing contact with a clean hydrochloric acid solution having an acid concentration of at least 18%, based on the weihgt of the solution, for a time sufficient to extract organosulfonic acid, separating the scrubbed product from the hydrochloric acid solution, and then stripping said scrubbed product at a temperature generally below that at which by-product sulfonic acid forms from the organosulfonyl chloride being stripped and under subatmospheric pressure of less than about 500 torr while an inert gas is caused to sweep the volatiles issuing from the organosulfonyl chloride during stripping.

DESCRIPTION OF THE INVENTION

This invention is a process, preferably continuous, for the removal of organosulfonic acids and volatile impurities from crude liquid organosulfonyl chlorides recovered from their manufacturing processes or contaminated by other means to a comparable extent.

The organosulfonyl chlorides which are treated in this process are those of the formula $RSO_2Cl$ wherein R is an alkyl group having from 1 to 12 carbon atoms. Examples of these R groups are methyl, ethyl, propyl, butyl, isobutyl, pentyl, hexyl, octyl and dodecyl. The preferred R group is a $C_1$ to $C_4$ alkyl group. Particularly preferred is methyl.

The scrubbing solution for the first treatment step of the crude MSC in this process must itself be substantially pure or free of the usual MSC process contaminants. The effective concentration of the aqueous hydrochloric acid scrubbing solution is from about 18 to about 36% HCl, based on the weight of the solution. Preferably, the concentration ranges from 30 to 36% in order to reduce significantly the hydrolysis rate of MSC with water. As used herein, the term "scrubbing" solution means a solution which, when intimately mixed with a crude MSC product, will solubilize unwanted by-product and allow the insoluble principal product to be collected free of unwanted contaminants. The term "scrubbing contact" as used herein means that the scrubbing solution is intimately mixed with the crude MSC product either as a static solution in a column or as a counter-current or, less preferably, as a concurrent stream of scrubbing solution and crude MSC.

The effective contact time of crude MSC in the scrubbing solution ranges from about 3 minutes to about 60 minutes. The preferred contact time is between 3 to 15 minutes.

The effective operating temperature of the scrubbing solution in the first step ranges from the freezing point to the boiling point of the hydrochloric acid solution (for 36% HCl the range is—17° C. to 110° C.). The preferred range is from about 0° C. to about 50° C. and, more preferably, from about 10° to about 25° C.

In bench or plant scale operation of this process, the scrubbing solution is employed in a first unit or scrubbing column. The scrubbing solution (a) removes MSA and its hydrates from the crude MSC, (b) prevents hydrolysis of the MSC by forcing the hydrolysis equilibrium in the direction of sulfonyl chloride by the presence of an excess amount of chloride ion; (c) reduces the solubility of the MSC in the scrubbing media by the ionic strength of the aqueous solution rendering the slightly polar MSC even more hydrophobic; and (d) can prevent eventual loss of MSC by using the scrubbing acid solution as feed to the reactor, thus allowing any suspended product in the scrubbing liquor to be collected in a typical decantation step.

Since the by-product MSA combines with up to three molecules of tightly-bound water, its presence during stripping requires the use of increased temperatures and a greater vacuum to force more of the loosely-bound water away from the MSA. Only under vigorous conditions, capable of decomposing the MSC, can the tightly-bound waters of hydration be split from the MSA. The removal of the by-product MSA prior to stripping results in the ability to remove water at a lower temperature at increased system pressures during the stripping operation.

Once the MSA is removed, mild stripping conditions must be employed to prevent additional hydrolysis of the MSC. Stripping is conducted in the second unit or stripping section of the process. The term "stripping" as used herein means an operation wherein the scrubbed MSC is delivered to one or more vessels capable of sustaining a vacuum pressure of as low as about 50 torr and a temperature of at least 100° C. when under vacuum and is subjected to stripping pressures and temperatures within the range for this invention.

The operating temperature of the vacuum stripper ranges from about 20° to about 70° C. The preferred temperatures are from about 40° to about 60° C.

In a plant operation of this process, the stripper section consists of two vessels in series. The first vessel operates at a temperature averaging about 70° C. and a pressure averaging about 230 torr while a nitrogen gas sweeps the volatiles. Most of the water in the MSC is removed in this first vessel before the MSC is passed to the second vessel. Because most of the water has been removed, the second vessel is operated at a temperature of 85°-95° C. and a pressure of 160-300 torr while nitrogen is bubbled through the MSC bringing some of the little remaining volatiles with it. This procedure postpones exposure of the MSC to the high temperature of the second vessel until almost all water is removed. This avoids the conditions which promote hydrolysis of the MSC to MSA, a substance which binds water and makes it more difficult to remove.

The operating pressure can be any reduced pressure which effectively removes the volatile impurities when using limited-efficiency vacuum sources. The usual operating pressure range for steam jets at 60° C. is about 200 to about 350 torr (consisting of water vapor pressure, 149 torr; residual volatiles and air sweep). In general, the operating vacuum pressure ranges from about 100 to about 500 torr.

During the stripping operation, an inert gas is caused to pass through (sweep) the volatiles issuing from the MSC product as it is being stripped. The gas may be any inert vapor but preferably dry air, nitrogen, or helium is used. The inert gas is caused to sweep in an amount sufficient to remove vapors of volatile contaminant being stripped from the MSC product. In general, at least about 0.5 unit volumes per minute of gas are used for each unit volume of MSC in the stripper. Preferably, between about 1 and 2 unit volumes per minute of sweep gas per unit volume of the MSC in the stripper vessel are used. The simultaneous stripping and sweeping operation is carried out for a time to remove an amount of by-product sufficient to provide the desired purity of the MSC product. In general, from about 3 to about 60 minutes will suffice.

The addition of a sweep of inert gas above the solution being stripped serves to carry out stagnant vapors of the volatile contaminants. The sweep of inert gas increases the stripper efficiency and enables a lower temperature to be used, as well as higher system pressures. A drop in the temperature of the MSC being treated from 80° C. to 50° C. reduces the hydrolysis rate constant of MSC, for example, at least 100 fold.

The following example is illustrative of the process of this invention.

EXAMPLE 1

A glass (scrubbing) column 2.5 cm. in diameter and 50 cm. long was charged with concentrated (36 wt. %) aqueous hydrochloric acid (HCl), 10 ml of crude methane sulfonyl chloride (MSC) containing 1,900 ppm (0.19% by weight) methane sulfonic acid (MSA) and 1,100 ppm (0.11% by weight) water, was added dropwise over a 60 minute period to the static column solution at 25° C. The MSC was kept at ambient temperature in contact with the concentrated HCl for 10 minutes. The MSC was easily decanted from the scrubbing column, appeared clear and contained <0.001% MSA and 0.2% water. No hydrolysis of the MSC was detectable during the scrubbing step.

The above procedure was repeated except that the scrubbing solution was replaced with an aqueous HCl solution at an acid concentration of 18% based on the weight of the solution. The MSC was easily decanted from the scrubbing column, slightly hazy and contained less than 0.001% MSA. The amount of MSA in the wash solution indicated that 0.1% hydrolysis had occurred at 25° C.

The decanted product obtained from the concentrated (36%) HCl scrubbing solution was placed into a rotating thin-film evaporator (stripper) filtered with a plastic tube for delivery of an inert gas stream just above the MSC being stripped. The MSC was subjected to stripping at a reduced pressure of 200 torr at 50° C. Clean, dry air was passed into the stripper through the tube at a rate of 1.4 liters/minute/liter of MSC in the stripper raising the total system pressure to 350 torr. The thin-film evaporator turned at a rate of 35 rpm. The recovered MSC contained <0.001% MSA and <0.011% water after 10 minutes contact time.

The above purification results contrast sharply with those found for an MSC product scubbed with concentrated (36%) HCl as described above, and then, after decantation, stripped for 10 minutes in a rotary thin-film evaporator rotating at 30 rpm. in the absence of a dry sweep gas, at a pressure of 250 torr and a temperature of 80° C. Under these conditions, the MSC product contained 0.13% MSA and 0.03% water. The high temperature used to drive-off the loosely-bound water from the MSA caused MSA by-product formation which was not removed during stripping.

EXAMPLE 2

A large scale operation used in an MSC manufacturing plant to purify the product MSC comprises (1) a Teflon-lined steel column 1 foot in diameter and 15 feet high as a scrubbing vessel and (2) a stripping section. The scrubbing column consists of a lower region of about 2 feet in height where the scrubbed MSC settles out, a middle packed section about 9 feet high containing packing consisting of one inch ceramic saddles, and an upper region of about four feet in height where used hydrochloric acid scrubbing solution collects and is removed.

The stripping section consists of two steam-heated glass pots connected in series. The first stripper is a 114 inch high column of which the bottom 30 inch high section is eight inches in diameter and the top 84 inch section is 6 inches in diameter. The bottom section has a glass steam coil positioned therein to heat the MSC being stripped. This stripper has an MSC inlet just above the 40% full level and an outlet on the other side at the column bottom. A one inch horizontal tube connects to the top of the stripper vessel for volatiles to be removed overhead and to provide for passage of a sweep gas with the volatiles. The second stripper is similar to the first stripper except that the top section is only 55 inches high providing a total column height of 85 inches. Because the volume of the second stripper is less than the first, its MSC inlet is just above the 50% full level but the outlet is also at the bottom of the column. In addition, the second stripper has a gas inlet at the bottom thereof to permit the sweep gas to bubble through the MSC during the final stripping stage. The sweep gas and volatiles from the second stripper are taken off through the one inch horizontal pipe at the top, pass through the pipe back over the first stripper, where the gas sweeps the first stripper volatiles, and the sweep gas and volatiles from both strippers are taken off overhead.

In operation, the scrubbing column was first completely filled with 31.5% concentrated, clean hydrochloric acid. Crude MSC containing from 0.1 to 2.0% water was passed into the column just above the packing at a rate of about 5 gallons per minute and the hydrochloric acid was continually pumped through a rotameter into the column from just below the packing at the rate of 1.5 gallons per hour. Droplets of MSC, at ambient temperature, fell down over the packing, making intimate contact with the hydrochloric acid, and the MSC, having substantially all MSA removed, formed a layer at the bottom of the column. The hydrochloric acid passed upwardly in contact with the falling MSC and out the top of the column.

Wet, MSA-free MSC passed from the bottom of the scrubbing column at the rate of 5 gallons per minute, through an automatic valve, and into the first stripper. In the first stripper, the temperature was maintained at about 70° C. and the pressure averaged about 230 torr. Under these conditions, over 90% of the water was boiled off and was taken off overhead with the aid of the nitrogen sweep gas. Passing into the second stripper, the MSC was subjected to about the same pressure as in the first stripper but to a higher temperature averaging about 90° C. to squeeze out substantially all water. In the second stripper, nitrogen was bubbled up through the middle of the column at the rate of 1 scfm (about 1.1 unit volume of gas per unit volume of MSC in each stripper section). MSC recovered from the second stripper contained less than 150 parts per million of water.

I claim:

1. A method of purifying a crude liquid organosulfonyl chloride product recovered from its manufacturing process or otherwise similarly contaminated which comprises first subjecting said crude product to scrubbing with a clean, aqueous hydrochloric acid solution having an acid concentration of at least about 18%, based on the weight of the solution, for a time sufficient to extract organosulfonic acid, separating the scrubbed product from the hydrochloric acid solution, and then stripping said scrubbed product at a temperature no greater than about 70° C. and under subatmospheric pressure of no greater than about 500 torr while an inert gas is caused to sweep the volatiles issuing from the organosulfonyl chloride being stripped, and thereafter recovering a purified organosulfonyl chloride product.

2. The method of claim 1 wherein the organosulfonyl chloride is a $C_1$-$C_4$ alkane sulfonyl chloride.

3. The method of claim 1 wherein the hydrochloric acid solution has a concentration of no less than 30%.

4. The method of claim 1 wherein the temperature of the acid solution is from about 0° to about 50° C.

5. The method of claim 1 wherein the organosulfonyl chloride residence time in the scrubbing solution is from about 3 to about 15 minutes.

6. The method of claim 1 wherein the stripping temperature is between about 40° and about 60° C.

7. The method of claim 1 wherein the total stripping pressure is no greater than 350 torr.

8. The method of claim 1 wherein the inert gas is air, nitrogen or helium at a partial pressure of less than 350 torr.

9. The method of claim 8 wherein the flow rate of the inert gas is no less than 0.5 unit volumes per minute per unit volume of the organosulfonyl chloride.

10. A method of purifying crude methane sulfonyl chloride product which comprises first scrubbing said crude product with a clean aqueous solution of hydrochloric acid at an acid concentration of from about 30 to about 36%, based on the weight of the solution, for about 3 to about 15 minutes, decanting the scrubbed methane sulfonyl chloride from the hydrochloric acid solution and subjecting the methane sulfonyl chloride to stripping at a temperature between about 40° and about 60° C. under a total pressure of no greater than 350 torr while sweeping the volatiles issuing from the methane sulfonyl chloride being stripped with an inert gas flowing at a rate no less than 1.0 unit volume per minute per unit volume of organosulfonyl chloride and providing a partial pressure of less than 350 torr.

11. The method of claim 10 wherein the temperature of the hydrochloric acid solution is from about 10° to about 25° C.

* * * * *